US007322929B2

(12) United States Patent
Lovoi

(10) Patent No.: US 7,322,929 B2
(45) Date of Patent: Jan. 29, 2008

(54) METHOD FOR RADIATION TREATMENT

(75) Inventor: Paul A. Lovoi, Saratoga, CA (US)

(73) Assignee: Xoft, inc., Fremont, CA (US)

( * ) Notice: Subject to any disclaimer, the term of this patent is extended or adjusted under 35 U.S.C. 154(b) by 568 days.

(21) Appl. No.: 10/464,140

(22) Filed: Jun. 18, 2003

(65) Prior Publication Data
US 2004/0260142 A1 Dec. 23, 2004

(51) Int. Cl.
*A61N 5/00* (2006.01)
(52) U.S. Cl. .......................................................... 600/3
(58) Field of Classification Search ................. 600/1–8
See application file for complete search history.

(56) References Cited

U.S. PATENT DOCUMENTS

| 6,251,059 | B1 * | 6/2001 | Apple et al. ................... 600/3 |
| 6,320,935 | B1 * | 11/2001 | Shinar et al. ................ 378/119 |
| 6,402,689 | B1 * | 6/2002 | Scarantino et al. .......... 600/300 |

FOREIGN PATENT DOCUMENTS

EP          105032        11/2000

OTHER PUBLICATIONS

Lerner, Eric J.; "Twenty Watts of Terahertz"; Apr./May 2003; p. 9-11; *The Industrial Physicist*.

"Development of Novel Technologies for In Vivo Imaging", Par-01-102, May 29, 2001; nih.gov website.

Tearney, Brezinski etal., "In Vivo Endoscopic Optical Biopsy With Optical Coherence Tomography" Jun. 27, 1997; *Science*, vol. 276, p. 2037-2039.

Toma, Tudor, "Oesophagcal Histology Without a Biopsy", Feb. 7, 2001; *The Scientist*, biomedcentral.com website.

"Surgical Technique of Intraoperative Radiotherapy in Conservative Treatment of Limited-Stage Breast Cancer", *Archives of Surgery*, vol. 137, Jun. 2002.

\* cited by examiner

*Primary Examiner*—John P. Lacyk
(74) *Attorney, Agent, or Firm*—Thomas M. Freiburger

(57) ABSTRACT

Breast cancer patients are treated intraoperatively with radiation shortly after excision of a tumor. Pathology of the tissue is determined with a nearly instantaneous method, further excision is performed if needed, and the patient, still anesthetized and preferably unmoved, is then treated with radiation therapy. In a preferred embodiment an applicator is inserted into the excision cavity, the cavity is three-dimensionally mapped using radiation sources and a sensor, a radiation treatment plan is developed using a radiation prescription and the determined shape and location of the cavity, and the treatment plan is executed, all while the patient remains under anesthesia.

51 Claims, 7 Drawing Sheets

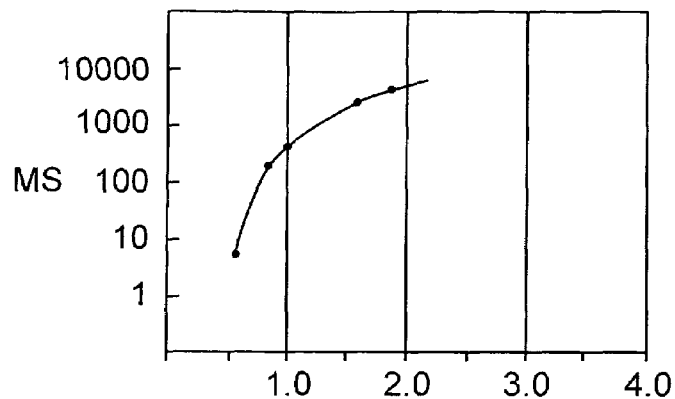
FIG. 7
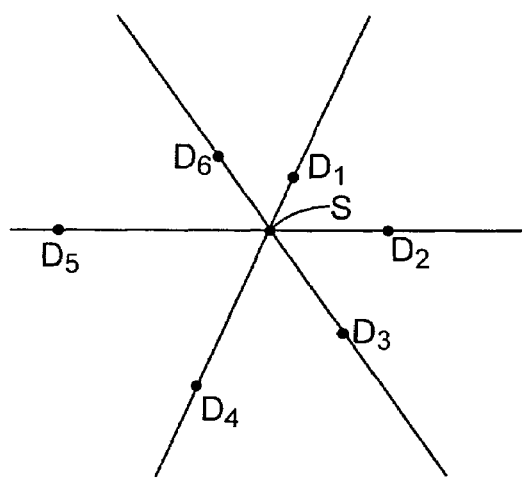
FIG. 7A
| SOURCE | DISTANCE | DOSE Gy/min | MS Time/1/10Gy |
|---|---|---|---|
| $D_1$ | .5 | 70 | 8.6 ms |
| $D_2$ | 1.0 | 8 | 750 ms |
| $D_3$ | 1.0 | 8 | 750 ms |
| $D_4$ | 1.5 | 2.5 | 2400 ms |
| $D_5$ | 1.75 | 1.7 | 3500 ms |
| $D_6$ | .75 | 20 | 300 ms |
FIG. 7B

METHOD FOR RADIATION TREATMENT

BACKGROUND OF THE INVENTION

This invention concerns the treatment of breast cancer or otherwise-sited cancer, and especially an efficient procedure for radiation treatment following surgical tumor excision, including pathology of the excised tissue, without waking or moving the patient or using external imaging techniques.

In treating cancer of the breast, as well as cancer found in other areas of the human body, with the patient under anesthesia, the tumor is surgically excised (with some surrounding tissue) and then typically, the surgical wound is closed, the patient is sent home pending determination of pathology of the excised tumor margin, a radiation treatment plan is developed, and the patient in a series of later visits is subjected to radiation treatment in the volume of tissue surrounding the excised tumor. This can often involve re-opening of the surgical cavity for insertion of an applicator for use with ionizing radiation sources, i.e. radioactive isotopes. The forming of a radiation treatment plan under these circumstances is usually a several-hour process that can require imaging of the excision cavity, to determine its shape and location in the body, using external devices such as magnetic resonance imaging or CT scanning equipment. Transfer of data is then needed between the imaging equipment and the treatment planning software for preparing a plan of irradiation, with the need to verify transferred data values to check for errors.

These several steps involve considerable time and associated costs and makes intraoperative radiation treatment logistically difficult if not impossible. In the case of breast tumors, moving of the patient for imaging is a problem in itself, because the breast is flexible and the excision cavity may move. There is a need for a methodology which would allow intraoperative radiation treatment of breast cancer and other cancers, without moving the patient, without requiring external imaging devices and without waking the patient from anesthesia.

There is also a need for increased precision in delivering radiation to a volume of tissue following surgery, to closely follow a physician's prescription. For example, more versatility and accuracy are needed in avoiding damage to skin in irradiation of breast tissue, and avoiding damage to the heart, lungs and bones, while still delivering prescribed dose where needed. Over-radiation of any tissue areas is to be avoided as much as possible.

Recent advances have occurred in determining pathology of a tumor, or of the surrounding tissue, almost instantaneously. See, for example, "Twenty Watts of Terahertz", Eric J. Lerner, *The Industrial Physicist*, page 9, April/May 2003. See also "Development of Novel Technologies for In Vivo Imaging", PAR-01-102, May 29, 2001, nih.gov website; "In Vivo Endoscopic Optical Biopsy with Optical Coherence Tomography", Tearney, Brezinski, et al., *Science*, Vol. 276, Jun. 27, 1997, pp2037-2039; "Oesophageal Histology Without a Biopsy", Tudor Toma, *The Scientist*, Feb. 7, 2001, biomedcentral.com website; "Determination of Spatial Location and Pathology of Breast Lesions using Proton MRS", imrr.org website; "Multiphoton Excitation Microscopy of Human Skin in Vivo: Early Development of an Optical Biopsy", Barry R. Masters and Peter T. C. So, optics.sgu.ru website.

Determination of pathology of tissue at the excision site is information the physician uses to determine whether further excision of tissue is required, or if the next step is radiation. The determination of a treatment plan depends on obtaining information on the shape and location of the excision cavity and the need to avoid damage to other areas of tissue (such as the skin, the chest wall, lungs and heart). Intraoperative radiation treatment has generally not been possible or practical for several reasons: the need to move the patient to the location of imaging equipment, to obtain the imaging data and transfer that data to a form useable in applicator equipment for performing the irradiation; and the need to obtain data on pathology of the excised tissue or the remaining tissue in the excision cavity, prior to executing a treatment plan. Obtaining these needed data requires considerable time; in general a patient following tumor excision should be ready for radiation treatment within about ½ hour, certainly less than 1 hour, and this is not possible with current procedures and equipment.

Proxima Therapeutics has developed a program for radiation treatment following tumor excision. In this procedure a breast tumor is excised, then an applicator is inserted into the excision cavity (often through a new incision at the time of tumor excision or up to several weeks later). The applicator is expanded and the incision is closed except for a pigtail or spigot extending out of the breast for later use. At a later date, following determination of pathology, if no further excision is indicated, the patient returns for radiation treatment via the applicator. The Proxima applicator is spherical and not capable of changing shape to accommodate irregularly-shaped cavities. The applicator comprises a balloon which can be filled to the appropriate size for the particular cavity, but beyond this size variation adjustment is not possible. The surgeon needs to cut as near-spherical an excision as possible to enable the proper use of the device. With the applicator in the excision cavity and filled, the patient's breast is imaged by exterior imaging equipment. This imaging not only determines the size of the inflated applicator within the breast excision cavity, but also enables the physician to look at any gaps between the applicator and the tissue at the boundaries of the excision cavity. Seroma from the wound may lie between the applicator and the cavity walls. 90% to 95% contact between the applicator and the excision cavity is required to ensure proper radiation delivery. If the applicator/tissue contact is sufficient, the physician uses a table to look up the needed dwell time for the diameter of the applicator and for the particular activity of the radio isotope source, which is known. The ionizing radiation source, i.e. an iridium ($^{192}$Ir) wire on the end of a stainless steel guide wire, is inserted into the middle of the applicator for the prescribed duration.

The Proxima procedure is based on a known geometry, i.e. a spherical shape of the applicator and cavity. The equipment is not adaptable to an irregularly-shaped excision cavity. Moreover, the applicator and procedure are not useful for smaller-sized tumors, because of unacceptable surface-to-depth ratio of radiation dose at near ranges of the radiation source.

The following patents and applications have some relevance to the present invention: European Patent Application EP1050321.

SUMMARY OF THE INVENTION

By the procedure of the present invention, intraoperative radiation treatment, in a practical sense, is enabled. Primarily this is achieved by (a) providing near-real-time data on pathology following the excision; and (b) immediate, on-site mapping of the shape and location of the excision cavity, all without waking or moving the patient. If pathology determination indicates to the physician that further excision is needed, this is done prior to the on-site mapping. A treatment plan is calculated from the three dimensional mapping data in a very short time, and the treatment plan is executed using the same applicator, the same applicator position and the same ionizing radiation sources as are used in the mapping, controlled by a processor. In a sense, the mapping step of the inventive procedure comprises a "trial treatment", providing accurate, useful data, with verification of the effects of each of a plurality of radiation sources in the applicator, including effects where radiation is not wanted, enabling accurate subsequent execution of the treatment plan.

The intraoperative procedure of the invention not only greatly improves accuracy in radiation treatment, but also subjects the patient to far less discomfort and trauma as compared to typical procedures. By the disclosed procedure the patient, while anesthetized in the operating room, is operated on to remove the tumor, the tumor is investigated as to pathology, by a very rapid process, decision is made as to any need for further excision (which is done if needed), the physician prescribes radiation dose for a volume of tissue surrounding the excision cavity, the shape of the cavity is mapped and recorded by internal measurements, calculations of radiation to be delivered at various sites in the cavity are made by use of the mapping data to thus prepare a treatment plan, and the treatment plan is carried out, all without waking or moving the patient, and all within a reasonable time.

In a preferred form of the invention, the procedure is applied to treatment of breast cancer. The tumor is excised from the breast, producing an excision cavity. While the patient remains under anesthesia, pathology is determined, further excision is made in the breast cavity if needed, and then the excision cavity is mapped using radiation sources, either isotopes or switchable x-ray sources. This is done using an expandable applicator, e.g. a balloon having a series of guides, the radiation sources being inserted into peripheral guides. A radiation sensor is placed into a central guide. The applicator is expanded to substantially fill the excision cavity, so that the peripheral guides are placed at walls of the cavity adjacent to a volume of breast tissue to be treated with radiation, such volume having been adjacent to the removed tumor. The excision cavity of the breast is mapped by moving the sources and sensor through the guides and determining dose at the sensor for each of the sources in turn at a plurality of locations along such movement, those locations being sufficient to substantially define the shape of the walls of the cavity. Dose received at the sensor for each source at each location is calculated into a distance from the source to the sensor, thus enabling a three dimensional wire-frame type map or model to be generated.

In a preferred embodiment sensors are also located outside the breast volume to be treated, on the breast surface and at the chest cavity wall (by needle), and these are monitored during mapping so as to locate the cavity within the breast.

The physician prescribes radiation treatment for the breast volume which surrounded the excised tumor, and from this prescription and from the derived three-dimensional map of the excision cavity, a radiation treatment plan is calculated for a volume to be treated immediately surrounding the excision cavity. The location of the cavity is important and the location data is used to avoid damaging radiation at the skin and at the chest wall. Computer software determines the treatment plan based on all this geometry.

Next, with the applicator remaining in position in the cavity and expanded as in the mapping step, the radiation treatment plan is carried out via movement and repositioning of the ionizing radiation sources within the applicator guides. Appropriate dwell times are used for the various locations, such that the prescribed dose of radiation is received in essentially all regions of the volume to be treated, without damaging sensitive areas such as the skin and chest wall. The sensors outside the breast can be used to monitor radiation actually received during the procedure at those sites, and/or as feedback to stop the procedure if excess dose is received or is predicted to exceed the prescribed dose.

In one preferred procedure, the ionizing radiation sources comprise switchable x-ray sources, variable as to voltage and current, as well as being switchable on/off during treatment, allowing the treatment plan to more accurately treat the prescribed volume without damage to sensitive areas. The sensors outside the breast volume to be treated are monitored to verify the accuracy of the procedure, and as noted above can actively feed back information to the processor controlling the treatment. With the controllable x-ray sources this feedback can be used to reduce depth of penetration of radiation from appropriate ones of the x-ray sources when needed.

It is therefore among the objects of the invention to improve radiation treatment of breast cancer and other malignant tumors, primarily by performing the radiation treatment intraoperatively, without moving or waking the patient, through the use of in situ three dimensional mapping of an excision cavity following surgery, using ionizing radiation sources and at least one sensor, and by using a method of instant pathology determination. Related objects are the mapping procedure itself, and the treatment itself, using controllable x-ray sources, preferably with real time monitoring with extra-cavity sensors. These and other objects, advantages and features of the invention will be apparent from the following description, considered along with the accompanying drawings.

DESCRIPTION OF THE DRAWINGS

FIGS. 7, 7A and 7B are a graph, a schematic view and a table indicating relationship of distance to time required to receive a preselected dose, as well the relationship of simply distance to dose.

DESCRIPTION OF PREFERRED EMBODIMENTS

Figure 1:
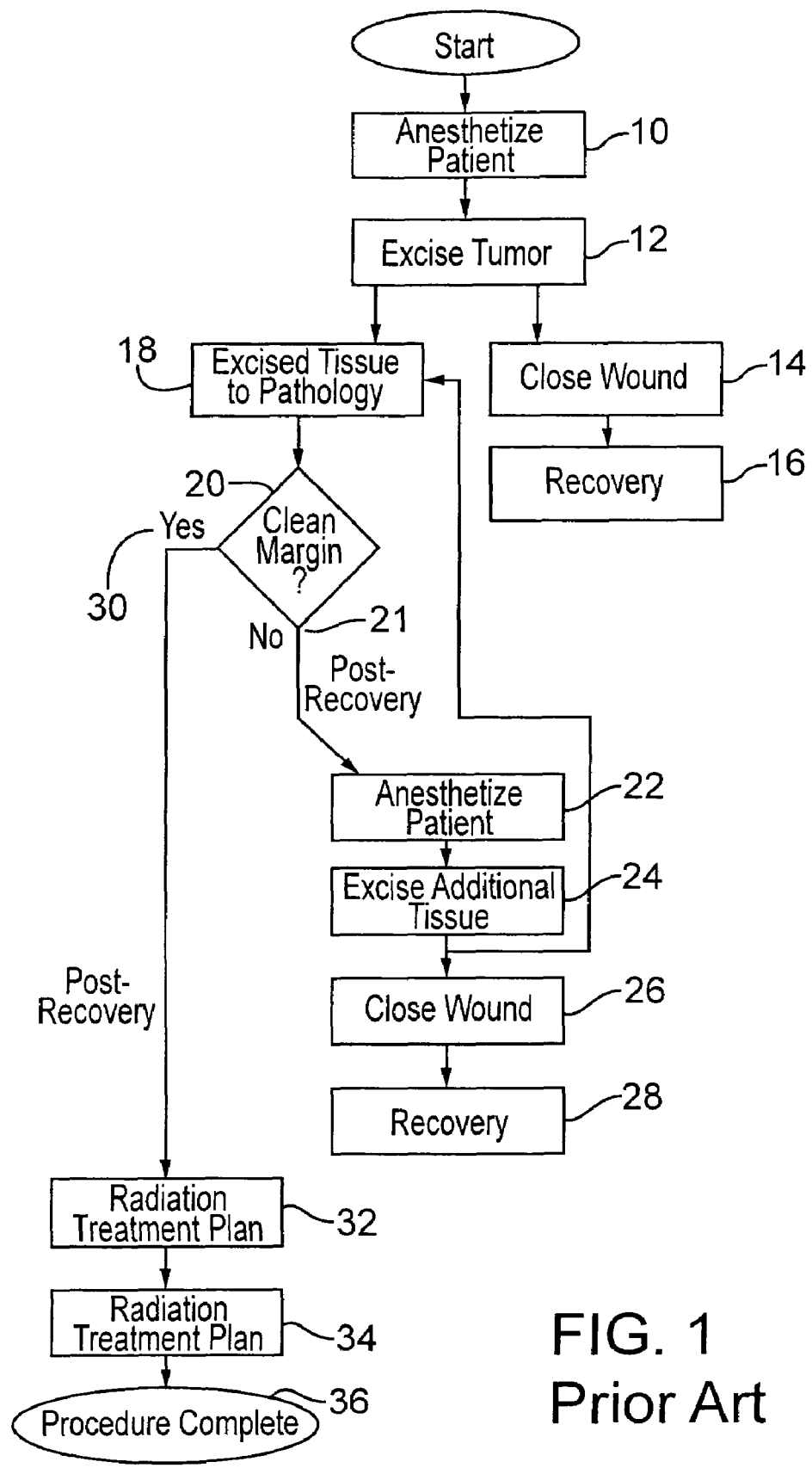
FIG. 1 is a flow diagram showing typical prior practice in excision of a tumor, determining pathology, and subsequent radiation.

FIG. 1 shows typical current practice, prior to the present invention, for excising a tumor, particularly from the breast of a patient, and the post-operative procedure. The patient is anesthetized as indicated at 10, and the tumor is excised as indicated at 12 in the drawing. Following excision, the surgical wound is closed as noted at 14, and the patient recovers as shown in the block 16 and is sent home.

Meanwhile, the excised tissue is sent to pathology as shown at 18, and the pathology of the tissue is determined as to whether there is a clean margin, as indicated at 20. As explained above, this takes some time. Different surgeons apply different standards as to whether a margin is sufficiently clean such that radiation treatment is judged to be sufficient to remove all remaining microfoci disease which might remain. If the physician decides the pathology of the tissue does not indicate a clean margin, as at 21, then further excision is deemed to be necessary. Thus, in this case, the post-recovery patient is again anesthetized at 22, additional tissue is excised, through the same or a different surgical wound, as at 24, and the excised tissue is again sent to pathology, as indicated by return to the block 18. The surgical wound is closed (block 26), and the patient again recovers from the surgery, indicated at 28, and is again sent home.

If, at the decision block 20, the surgeon decides the excised tissue exhibits a clean margin (30), then a radiation treatment plan is prescribed and calculated, as noted in the block 32. Then the patient, after recovery (at 16 or 28) is treated with radiation according to the treatment plan, as indicated at 34. At 36 completion of the procedure is indicated.

In this traditional practice, the radiation treatment plan is derived from (a) a prescription which typically involves a standard dose of radiation at a standard prescribed depth in the tissue surrounding the excision cavity in the patient, (b) imaging of the excision cavity, by external imaging devices such as x-ray, ultrasound or CT scanning equipment, to determine the size and shape of the cavity and its location within the breast, and (c) use of the imaging data in the treatment planning software, which depends on accurate transfer of data between the imaging equipment and the software. Accuracy can be difficult, as explained above in the case of breast surgery, since the patient must be moved to the imaging facility and the breast comprises flexible tissue and may move, causing the location of the excision cavity to move and change in shape.

Figure 2:
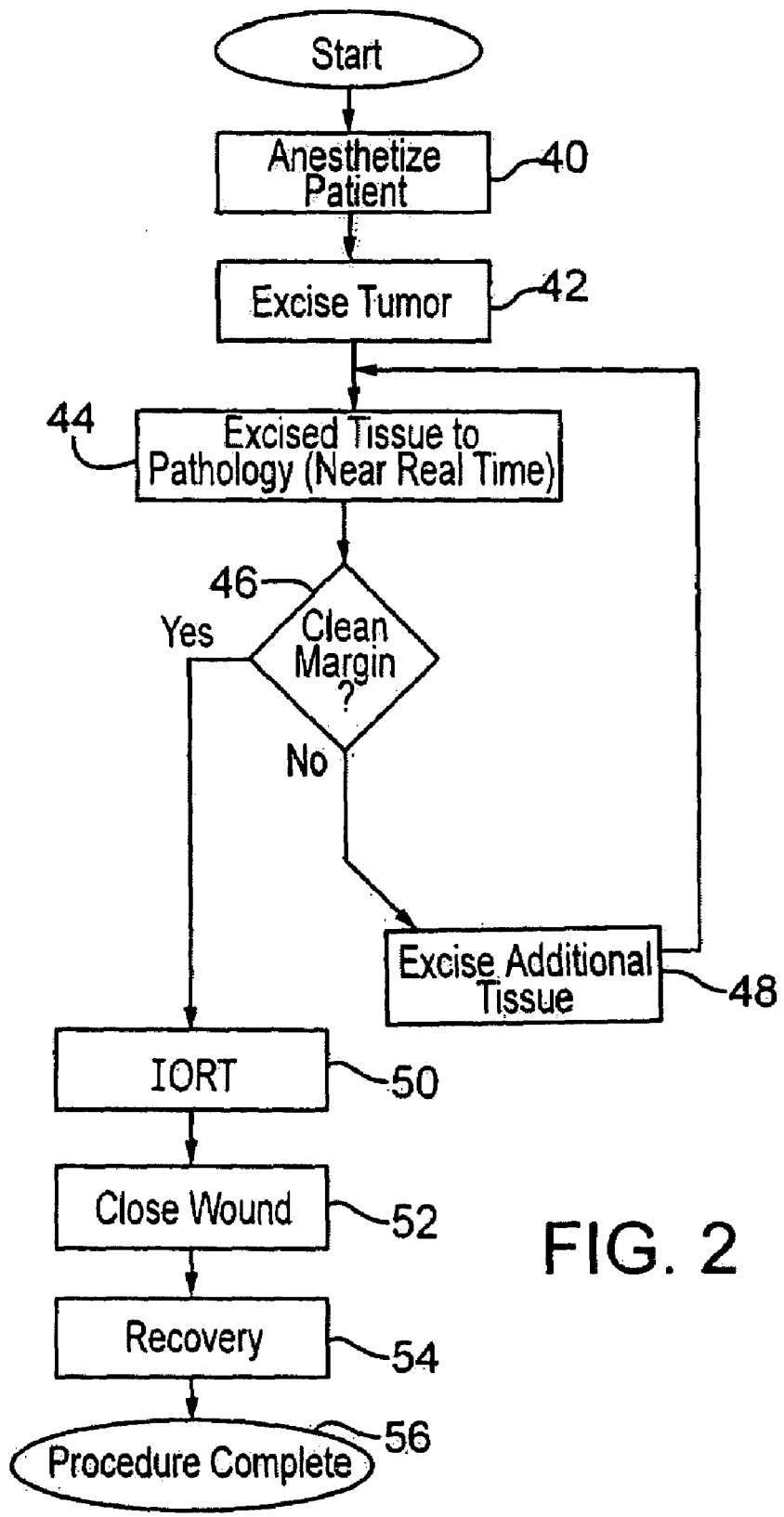
FIG. 2 is a flow diagram outlining a procedure in accordance with the invention.

FIG. 2 is a flow chart showing the main elements of a procedure according to the invention for intraoperative radiation treatment associated with excision of a tumor. The patient is anesthetized at 40 and the tumor is excised at 42, as in the prior procedure. The excised tissue is taken to pathology (block 44), and as noted in the decision box 46, it is determined through pathology whether the tissue exhibits a clean margin. This is accomplished with a near-real-time method of pathology, as discussed above, without waking and preferably without moving the patient. Such methods are discussed above.

If it is determined from the near-instantaneous method of pathology that the excised tissue (or the wall of the excision cavity) does not exhibit a clean margin, then the surgeon proceeds to excise additional tissue, indicated at 48. This may be through the same or a different surgical incision. With this completed, the tissue is again examined by a near-instantaneous method of pathology, and the results are used to determine whether the tissue exhibits a clean margin.

If a clean margin is determined, the process proceeds to IORT, intraoperative radiation therapy, shown at 50, according to a calculated treatment plan. After the radiation treatment, the wound is closed (52), the patient is allowed to recover, indicated at 54, and the procedure is complete (block 56).

Figure 3:
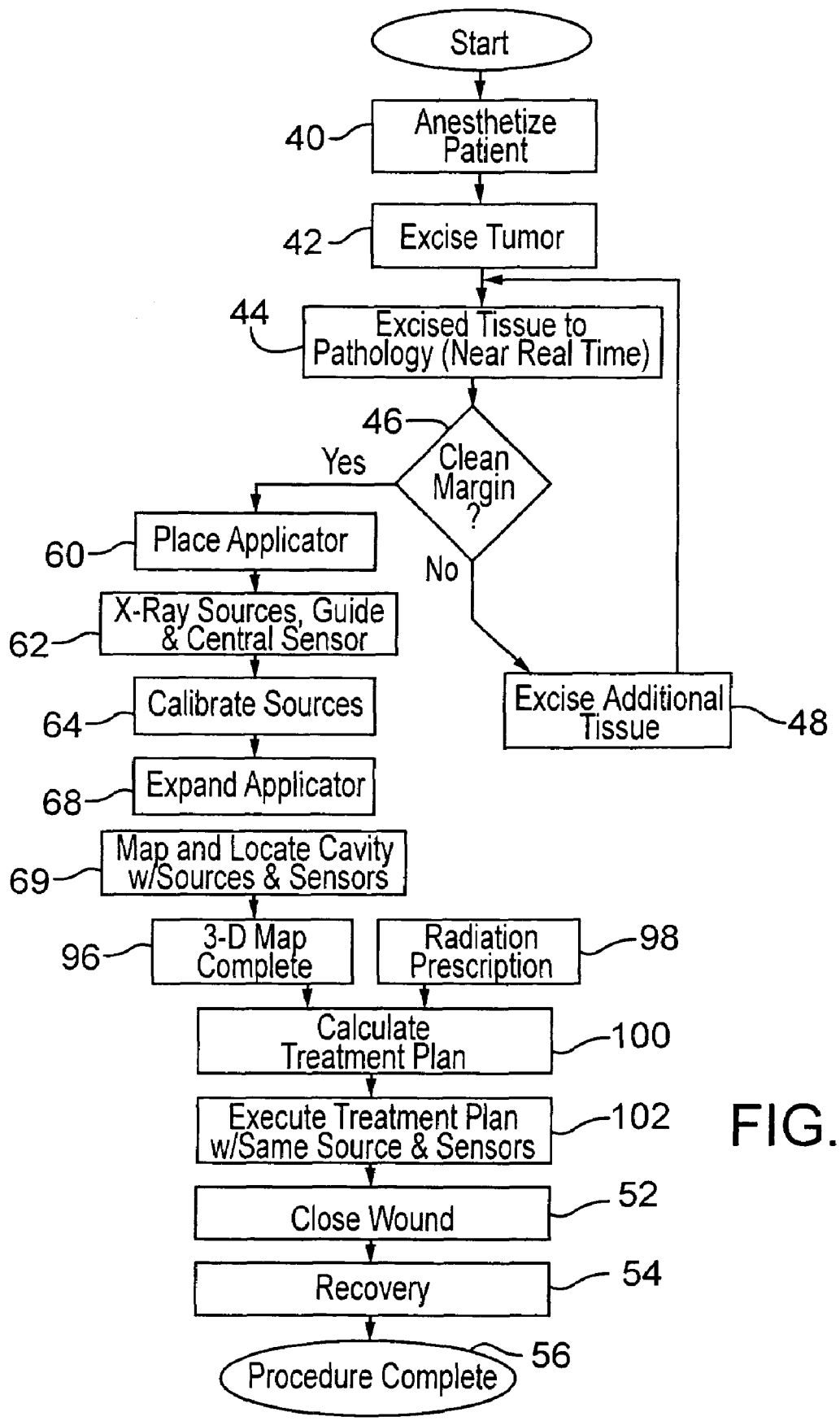
FIG. 3 is a flow diagram in greater detail, representing a preferred embodiment, including a three-dimensional mapping procedure.

FIG. 3 is a more detailed flow chart, showing additional steps in a preferred procedure for intraoperative radiation therapy according to the invention.

Steps 40, 42, 44, 46 and 48 are the same as described above with respect to FIG. 2. Once a clean margin is determined, which might be after additional excision of tissue while the patient remains anesthetized as described above, an applicator is placed into the excision cavity, as noted at 60. The applicator may be a balloon type device or other expandable applicator having guides for receiving x-ray sources and, in this case, a guide for receiving an x-ray sensor placed generally centrally. Once the applicator has been placed in the excision cavity, in a preferred embodiment x-ray sources are inserted into guides which will ultimately be expanded against the walls of the cavity, and a sensor is placed in the central guide, as indicated in the box 62. Then the sources are calibrated (as at 64), with the applicator collapsed and with the sources closely adjacent to the central sensor. This is shown schematically in FIG. 4, the guides containing the sources being shown at 65 and the central guide with the sensor being at 66. The later expanded positions of the guides 66 are shown at 65a, against the wall 67 of the excision cavity.

With this calibration data taken in the collapsed state as to the radiation emanating from each of the sources as read at the adjacent sensor, differences in the sources and relative values can be determined such that once the applicator is expanded, doses read at the central sensor from each source can be used accurately to calculate distance.

Figure 4:
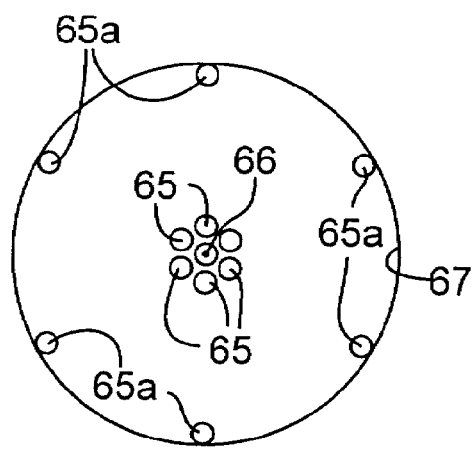
FIG. 4 is a schematic view indicating a step for calibrating radiation sources prior to mapping and prior to treatment.

With the sources calibrated, the applicator is expanded as indicated at 68 in the flow chart and at 65a in FIG. 4.

Figure 5:
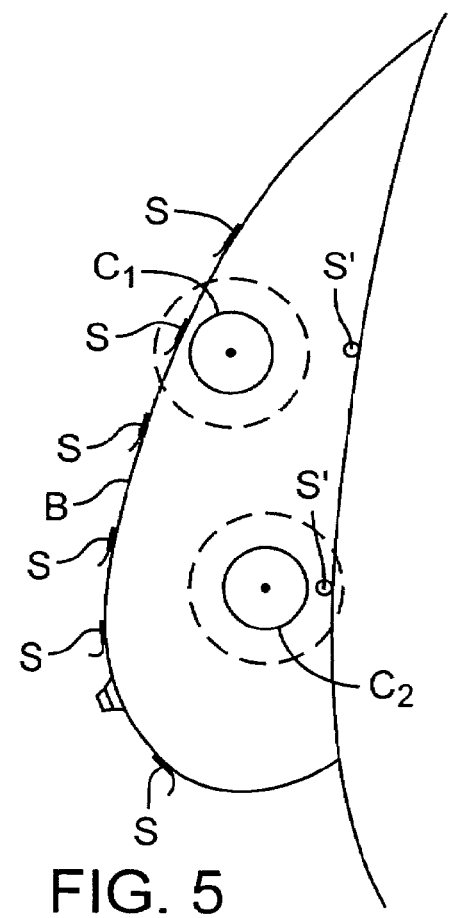
FIG. 5 is a schematic view in sectional elevation indicating several possible locations of excision cavities in a breast, surrounded by a volume to be treated and indicating depth of prescribed radiation in the volume to be treated, and the intersection of the prescription radiation volume with the skin and chest wall, and also indicating use of sensors on the breast and elsewhere outside the cavity for locating the cavity and for feedback.

The expansion of the applicator locates the x-ray source guides directly against the walls of the excision cavity (FIG. 4), with the sensor guide remaining in a generally central location (66 in FIG. 4). Preferably, additional sensors have been placed at other strategic locations as discussed above: in the case of the breast, on the exterior surface of the breast, and preferably also at the chest wall, via a needle. These sensors are used to locate the excision cavity during the mapping step to be described below, as well as providing a means for quality control, and possibly emergency shutoff, during the radiation treatment. FIG. 5 shows schematically, in the case of a breast B, sensors s located on the exterior surface of the breast, preferably arrayed laterally as well as in vertical separation as shown, and sensors s' inserted via needle at the chest wall. This is discussed further below.

With the applicator expanded and the sensor or sensors in place, the three dimensional mapping begins as indicated at 69 in FIG. 3. The patient remains in the same position and anesthetized, and x-ray sources, which may be switchable, e.g. small x-ray tubes, or an isotope source, are placed in the guides of the applicator. With the x-ray sensor located in the generally central guide, the sources and sensor in the guides are pulled back in a series of steps from the distal end of the excision cavity to the proximal end, in approximately five to ten different longitudinal positions of the cavity (i.e. positions along the length of the applicator guides). In the case of switchable x-ray sources, each source may be switched on for a set, short period of time, and the dose read at the central sensor. Alternatively each source may be switched on at maximum voltage for maximum penetration, and switched off automatically when a preselected dose of x-rays is detected at the sensor. The duration of time is then used to calculate distance, as discussed below in reference to FIGS. 6 and 7. In either event this is done in succession for the plurality of sources placed around the walls of the cavity, e.g. about two to ten sources (different numbers can be used). In this way, a unique reading is obtained for each source position, and this is repeated at the plurality of longitudinal positions in the cavity as noted above. Each dose value (or time duration) is translatable into a distance, and thus a three dimensional map of the incision cavity's interior is obtainable.

In the case of isotopes, only a single isotope is generally used at one time, placed first in one guide, where all readings are taken in succession, then in the next guide, and so on. Different isotopes can be used but preferably not inserted simultaneously.

Figure 6:
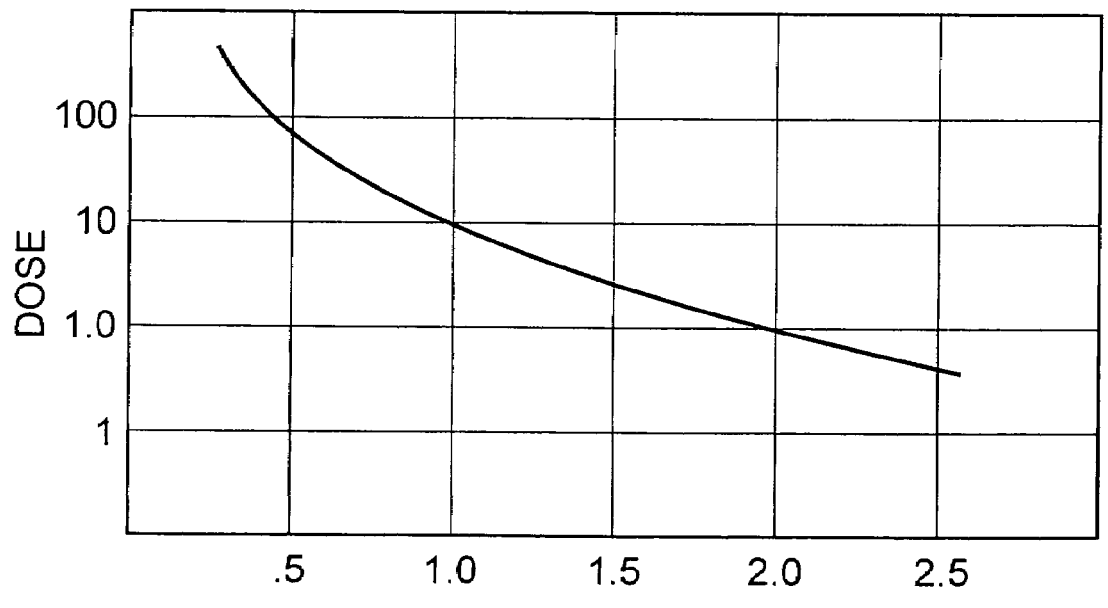
FIG. 6 is a graph showing radiation dose vs. distance from source.

FIGS. 6, 7, 7A and 7B demonstrate calculation of the shape of the cavity wall by the method described above. In FIG. 6, dose is indicated as a function of distance from the sensor. The vertical or y axis is a logarithmic scale. As indicated, dose falls off very rapidly with distance, not only due to the inverse square law ($1/r^2$) but also taking in the effects of attenuation of radiation passing through tissue absorption. For example, FIG. 6 shows that doubling the distance from the sensor, from about 0.5 cm to 1.0 cm, drops the dose approximately by a factor of nine, and from 1 cm to 2 cm, by an approximate factor of ten. The chart in FIG. 6 represents the dose from an x-ray source operating at 45 $kV_p$.

FIG. 7A schematically shows a possible location of six different x-ray sources $D_1$ through $D_6$, in positions against the wall (not shown) of an excision cavity. A sensor s is shown in a generally central position. As schematically indicated, each of the sources is a different difference from the sensor s. FIG. 7B shows an example of dose versus distance for the six sources $D_1$ through $D_6$. The information under "distance" and "dose" is as taken from the graph of FIG. 6. However, the right column in FIG. 7B corresponds to FIG. 7, which is the time duration to receive a specified dose, e.g. 0.1 Gy (as is well known 1 Gy=100 rad). FIG. 7 is a graph showing this form of distance mapping, with milliseconds on the vertical axis and distance on the horizontal axis. As discussed above, minimal radiation of the patient during mapping can be achieved by turning the switchable radiation sources to a high voltage setting and maintaining that setting for each source position, shutting off the source whenever a preselected dose is reached, such as 0.1 Gy. Note that 0.1 Gy, which is 10 rad, is a more than adequate level of radiation for detection by the central sensor and also sensors located outside the breast, as in FIG. 5. The graph of FIG. 7 illustrates how distance is determined, by an algorithm.

Returning to FIG. 5, the sensors s and s' are located on the surfaces of the breast and at the chest wall, to monitor radiation and also to locate the three dimensional cavity map relative to these locations. The surface mounted sensors s, as shown in FIG. 5, may fall within the prescribed volume to be treated. This is the case with the upper cavity $c_1$; the lower cavity $c_2$ has the chest wall sensor s' located within its prescription dose volume. During the mapping procedure, these sensors determine that the skin or chest wall is within the prescription dose region, and that the skin or the chest wall may receive a dose exceeding that desired by the physician. Excessive doses at these structures can lead to damage—in the case of the skin, poor cosmesis outcome, and in the case of the chest wall, possible damage to lungs, heart, great arteries and bone. Thus, the decision is made, either by the physician or the radiation oncologist, or by the computer program, as to whether the prescription dose should be maintained or whether the issue of damage to these other structures should dominate the treatment plan. With the switchable x-ray sources which are preferred according to this invention, this issue is much more easily and more accurately handled. The x-ray sources can be switched on and off, and/or their voltage can be varied when nearing the surface, to lessen penetration. Moreover, the sensors s, s' can be used to monitor the treatment plan's accuracy and effectiveness, by measuring dose actually received at those structures during treatment. As noted above, voltage can be varied in real time during the treatment, in accordance with such detection.

In addition, and importantly, the sensors s and s' can be used to verify the total dose received in all regions, by calculation in the software which accurately extrapolates the total dose received at all locations. Is it not necessary that a sensor be located directly in the prescription volume as in FIG. 5.

Figure 5A:
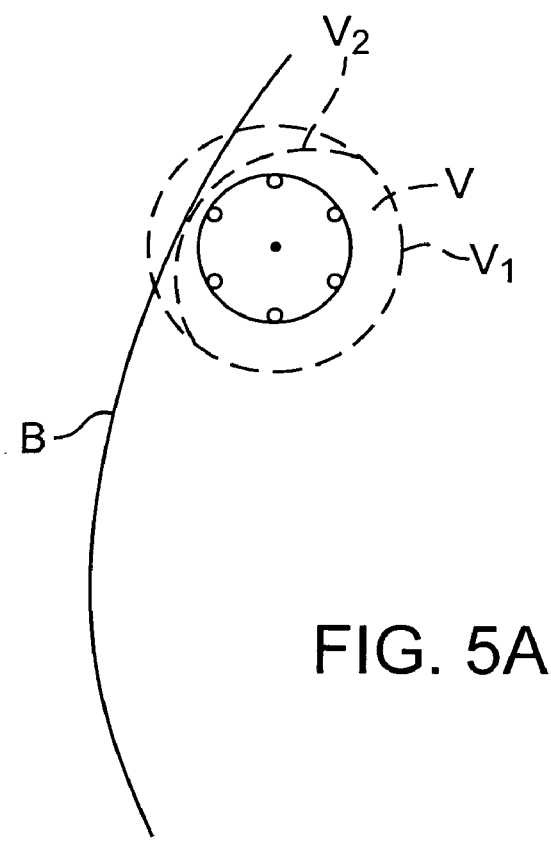
FIG. 5A is a schematic view showing a portion of FIG. 5 and showing limitation of radiation at the skin according to prior practice.
Figure 5B:
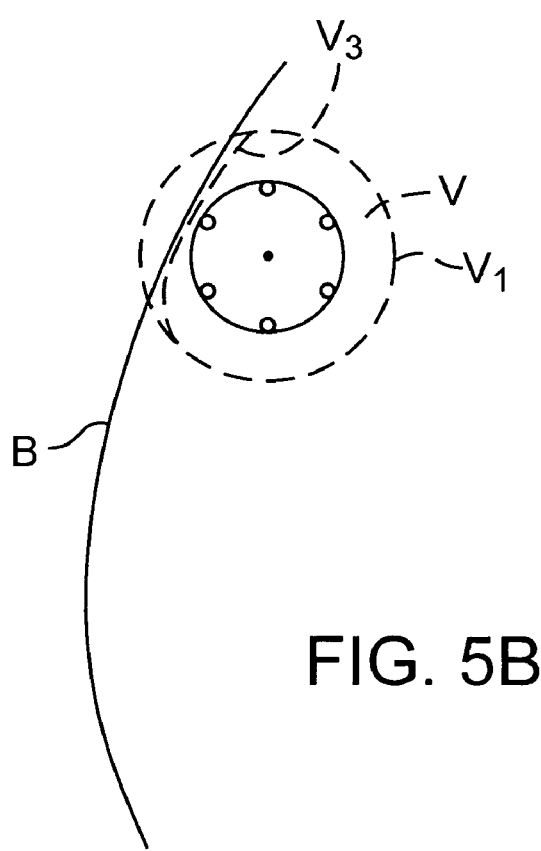
FIG. 5B is a view similar to FIG. 5A showing limitation of radiation penetration achievable with the invention.

FIGS. 5A and 5B demonstrate that use of switchable and variable sources, e.g. switchable x-ray tubes, enables far greater flexibility in treating a very specific prescription volume. Using the example of the breast, FIG. 5A again shows, as in FIG. 5, the situation where a prescription volume to be treated intersects with the exterior breast surface B. As explained, this is objectionable and often unacceptable with the potential to do severe damage to the skin. The dashed line $V_1$ defining this volume to be treated is an isodose curve, basically a three dimensional surface. A treatment plan must integrate the doses received from each of the many sources at all of the dwell points, optimizing the dose at every point within the volume to be treated and eliminating potentially damaging radiation at boundaries such as the breast surface. This is a complex algorithm but is typically accomplished, as best possible, for isotopes having a fixed TG-43 profile. The algorithm takes into account angles relative to each source, and the fall-off of dose with depth and with angle. In FIG. 5A the modified curve $V_2$ is an optimized isodose curve based on the best that can be accomplished using merely the limitation of dwell time in the treatment plan. This shows approximately how the isodose curve would change if the dose at the skin were limited so as not to exceed the prescription dose. As shown in the schematic approximation of FIG. 5A, the skin boundary is not overlapped with the prescription dose by the curve $V_2$, but at the same time, other areas within the prescribed volume are not given the prescription dose, i.e. these regions are underdosed.

FIG. 5B, a schematical view similar to FIG. 5A, shows approximately what can be achieved using the invention and the preferred switchable, variable x-ray sources. Again, the isodose curve V, intersects with and overlaps the breast surface B. Here, however, the x-ray sources are switchable and variable as to at least voltage and preferably also current. The treatment plan algorithm takes this into account and optimizes, for all regions of the volume V to be treated, the dose that will be received, with the sources varied as to voltage for varying depth of penetration, and also as to either current or dwell time (current and dwell time are equivalent). The dwell time is varied by switching these sources on/off, while reduction of current is another way to reduce dose. The modified curve $V_3$ in FIG. 5B approaches very closely the skin, as is desired, through virtually the entire range of the volume V to be treated inside the breast. This is achieved by a complex algorithm that calculates the treatment plan, with the ability to vary both dwell time (or current) and voltage (depth of penetration).

As noted above, an algorithm to achieve this complex prescription isodose surface must involve the integration of the effects of all sources at all positions. Every dwell point of a source affects every point within the volume to be treated and surrounding points. If, for example, six sources (i.e. guides) are used in the applicator, and ten different dwell points are used in each guide, this produces sixty different dwell points, the effects of each of which must be integrated to the treatment plan as to the effect at every point reached by the radiation. This is a difficult problem but can be solved, with the appropriate algorithm, and the ability to achieve the desired treatment plan is made possible by the use of sources which are variable as to voltage, i.e. depth of dose.

The treatment described could be accomplished with continuous movement of the sources and sensor, with such movement taken into account in the algorithm and rate (or varying rates) of movement being a part of the treatment plan. It is also possible to perform three-dimensional mapping using moving sources, but this may be undesirable if the sources are continuously emitting radiation, since this can lead to excessive doses of radiation during mapping, or when mapping radiation is accumulated with treatment radiation. Development of more sensitive sensors could make moving mapping more desirable, with less radiation emitted. In the claims, references to moving the sources and sensor to a plurality or positions or locations, or references to taking readings at various locations should be understood to include continuous movement as well as a series of stops.

It should also be understood that the calculation of a radiation treatment plan can take into account radiation already received during mapping in the volume to be treated. Once the cavity shape and location are determined, the radiation dose at each location, received during mapping, can be calculated. If mapping radiation is limited so that the mapping dose is comparatively extremely small, this dose can generally be ignored.

Figure 8:
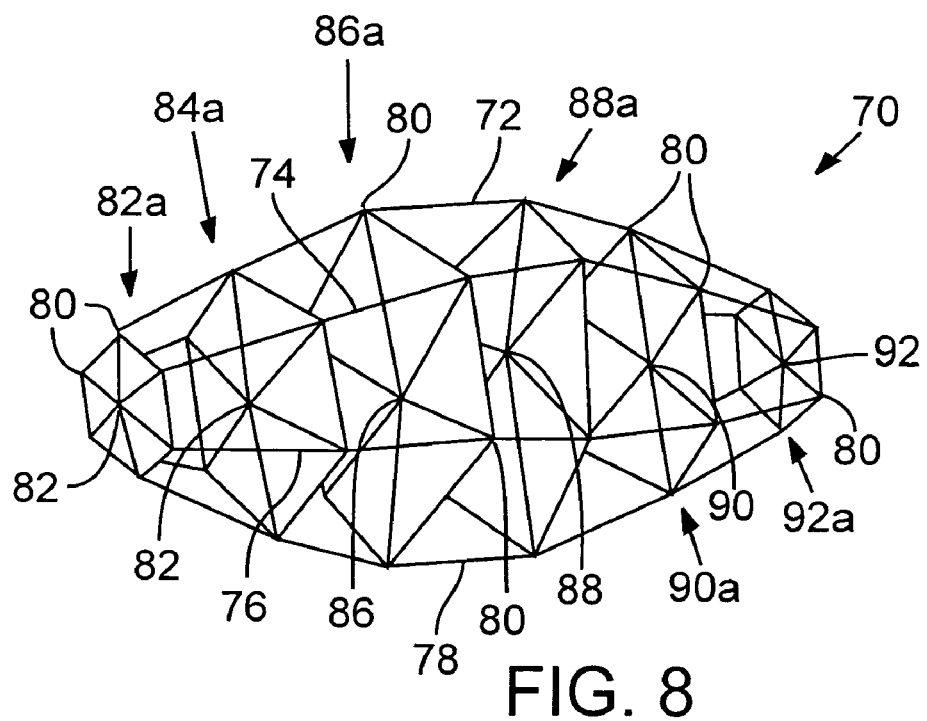
FIG. 8 is a schematic view in perspective, showing a wire-frame model of an excision cavity.

FIG. 8 shows an example of a wire-frame type three dimensional map 70 that can be obtained using the mapping procedure of the invention. Outer longitudinal lines 72, 74, 76, 78, etc. of the wire frame model or three dimensional map represent the approximate positions of the guides in the cavity. Nodes 80 on each of the lines 72, 74, 76, etc. are at the locations of the guides where readings were taken from the sources there positioned, i.e. dwell points. The series of location points for the sensor are indicated at 82, 84, 86, 88, 90 and 92. The dwell points or nodes 80 are all in the same plane with one of the sensor location points 82, 84, 86, etc. All measurements are taken one plane at a time, with the central measurement sensor and the x-ray sources within that same plane during that measurement. As noted earlier, in the case of isotopes typically only one isotope is used, positioned successively in each of the guides, so that each planar dwell point is within the same plane after all readings are taken for that plane. In other words, in each plane of measurement, the sources are advanced to the same point, such that they all lie in the same plane with the sensor. Readings are taken sequentially rather than simultaneously, and for isotopes this involves repositioning to each of the different dwell points within each plane (although the order of the dwell points need not be to complete one plane before undertaking the next). For switchable sources, the series of sources preferably are simultaneously in place, but are sequentially turned on. It should be understood, however, that for switchable sources a single source could be used if desired, and for isotopes multiple sources could be used, although preferably not inserted into the excision cavity at the same time.

Each of the sensor points 82, 84, 86, etc. is roughly near the center of a plane, of which six such planes 82a, 84a, 86a, 88a, etc. are shown in FIG. 8, one for each reading location. It can be appreciated that merely having the data of the distance from the center or sensor point of each such wire plane to each of the plurality of surrounding points (six in the illustrated embodiment) will provide the dimensions of the plane, but will not locate that plane relative to the next and succeeding planes. One plane may be laterally displaced from the other planes, i.e., the sensor points 82, 84, 86, etc. may not be in a single line and perhaps not on a single smooth curve. Further, some of the planes could be rotated about the sensor point 82 or 84 or 86, etc. relative to other such planes, if the guides follow slightly tortuous paths. The additional data needed to locate these planes precisely relative to one another can be provided in one of two ways: by use of an applicator with a relatively rigid and linear central guide, and with peripheral guides that expand in a manner such that each particular curving guide lies in a single plane; or using data from the additional sensors placed outside the cavity, e.g. at the breast surface and along the chest wall, as described above. These additional sensors will provide distance data that will locate the planes relative to one another, and also locate the excision cavity itself (i.e. the wire frame model 70) within the breast or other patient tissue.

In FIG. 3 the three dimensional mapping is indicated as completed in the block 96. These data, along with a radiation prescription (98), i.e. desired dose and depth for the patient tissue surrounding the excision cavity, are used to calculate a radiation treatment plan 100. The calculation of the treatment plan takes into account the distance to the surface-located sensors and to the chest wall, in the case of a breast to be treated, since radiation must be limited at the skin to prevent damage, and also at the chest wall. The calculation will take this into account, lessening the depth of penetration of the total radiation in the regions of these locations. This is achieved far more easily using switchable x-ray sources, and preferably sources which are not only switchable on/off but also with voltage control and current control.

With the treatment plan calculated, it is executed using the same sources and sensors, as indicated in the block 102. At this point the exterior sensors, outside the excision cavity, can be used to monitor radiation dose actually received. This can be used for emergency shutoff, or simply for quality control of the procedure, verifying the actual treatment was according to plan.

Figure 9:
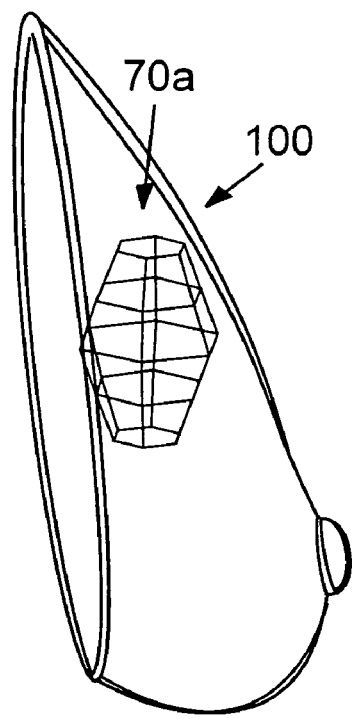
FIG. 9 is a schematic perspective view of a breast indicating an excision cavity in the form of a wire-frame map or model as in FIG. 8.

FIG. 9 is similar to FIG. 8 but shows a three dimensional wire frame model as it might be located within a breast 100. The wire frame model is shown at 70a, oriented within the breast tissue. As in FIG. 5, the sensors can be located at the exterior of the breast and at the chest wall, not shown in FIG. 9.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. A method for intraoperative radiation therapy treatment in a living patient, comprising:
    following excision of a tumor from a patient, while the patient remains under anesthesia, mapping the excision cavity by the steps of:
        (a) inserting an applicator into the excision cavity, the applicator including a series of guides,
        (b) inserting one or more ionizing radiation sources into peripheral ones of the guides and inserting a radiation sensor into a central one of the guides,
        (c) expanding the applicator to substantially fill the cavity, thereby placing the peripheral guides substantially at walls of the cavity adjacent to a volume to be treated with radiation,
        (d) moving the sources and sensor through the guides and taking a reading with the sensor for each of the sources at a plurality of locations along such movement, such locations being sufficient to substantially define the shape of the walls of the cavity,
        (e) from data determined in step (d), determining a three-dimensional model of the excision cavity,
    using a radiation prescription prepared by an attending physician, making a radiation treatment plan for a volume to be treated immediately surrounding the excision cavity based on the three-dimensional model of the cavity, while the patient remains under anesthesia and the applicator remains within the incision cavity, for irradiation of the volume to be treated by use of such ionizing radiation sources and the applicator, and
    executing the treatment plan by moving the ionizing radiation sources through the peripheral guides of the applicator with appropriate dwell times such that substantially the prescribed dose of radiation is received in all regions of the volume to be treated.

2. The method of claim 1, wherein the ionizing radiation sources are switchable x-ray sources.

3. The method of claim 2, wherein the switchable x-ray sources during execution of the treatment plan are varied in voltage to adjust depth of x-ray penetration at different locations.

4. The method of claim 2, wherein some of the x-ray sources are maintained at different voltage from others during execution of the treatment plan, so as to deliver radiation to different depths in different locations.

5. The method of claim 2, wherein at least some of the switchable x-ray sources are varied as to current during treatment, for variation of dose density at different locations in the volume to be treated.

6. The method of claim 2, wherein, during treatment, some x-ray sources are operated at different current than other x-ray sources, in order to deliver different dose density at different locations, according to need based on the radiation treatment plan.

7. The method of claim 2, including switching off one or more of the x-ray sources during treatment when needed in order to follow the radiation treatment plan.

8. The method of claim 1, wherein the ionizing radiation source or sources are isotopes, which are removed after mapping and reinserted into the applicator for execution of the treatment plan.

9. The method of claim 1, further including, prior to the mapping step, pre-calibrating the ionizing radiation sources by clustering the sources closely around the radiation sensor and determining dose received from each source using the sensor.

10. The method of claim 9, wherein the ionizing radiation sources are switchable x-ray sources.

11. The method of claim 9, wherein the ionizing radiation sources are isotopes.

12. The method of claim 1, further including obtaining pathology from the excised tumor, and, if a clean margin is not indicated, re-excising before mapping the excision cavity, all while the patient remains under anesthesia.

13. The method of claim 12, wherein the step of obtaining pathology from the tumor comprises use of an instant method of pathology determination.

14. The method of claim 1, wherein the ionizing radiation sources are switchable x-ray sources, and wherein step (d), taking a reading with the sensor, is accomplished by operating the sources at a high voltage level and measuring, via the sensor, the duration of time required for the sensor to detect a preselected dose for each source at each location.

15. The method of claim 1, wherein step (d), taking a reading with the sensor, is accomplished by determining dose received at the sensor from each of the sources over a preselected period of time.

16. The method of claim 1, further including placing extra-cavity sensors outside the cavity in critical areas where radiation dose must be limited to avoid damage, and during execution of the treatment plan, monitoring dose received at such extra-cavity sensors to assure that dose is limited in the critical areas.

17. The method of claim 16, wherein the excision cavity is within the patient's breast, and said extra-cavity sensors are located on the skin of the breast.

18. The method of claim 17, wherein at least one said extra-cavity sensor is located at the chest wall, via a needle.

19. The method of claim 1, wherein prior to mapping of the cavity, extra-cavity sensors are placed outside the cavity in critical areas where radiation dose must be limited to avoid damage, and during mapping of the excision cavity, readings are taken at each extra-cavity sensor from the sources at said plurality of locations, and data from such readings are used to modify the radiation treatment plan so as to limit dose as needed at such critical areas.

20. The method of claim 19, further including, during execution of the treatment plan, monitoring dose actually received at such extra-cavity sensors to assure that dose is limited as needed in the critical areas.

21. The method of claim 19, including calculating dose received during mapping at various locations inside and outside of the volume to be treated, and taking such already received dose into account in making the radiation treatment plan.

22. A method for intraoperative radiation treatment of breast cancer in a living patient, comprising:
    following excision of a tumor from a patient's breast, while the patient remains under anesthesia, determining pathology of the tissue at the excision margin by a near-real-time method of pathology determination,
    if indicated by pathology, further excising tissue at the excision cavity, while the patient remains under anesthesia, and
    irradiating a volume of tissue adjacent to the excision cavity, thereby performing pathology and radiation intraoperatively, while the patient remains under anesthesia following tumor excision and is essentially unmoved.

23. A method for three-dimensional mapping of a cavity in a human body, comprising:
   (a) inserting an applicator into the cavity, the applicator including a series of guides,
   (b) expanding the applicator to substantially fill the cavity, thereby placing the peripheral guides substantially at walls of the cavity adjacent to a volume to be treated with radiation,
   (c) with one or more ionizing radiation sources in peripheral ones of the guides and with a radiation sensor in a central one of the guides, moving the sources and sensor through the guides and taking a reading with the sensor for each of the sources at a plurality of locations along such movement, such locations being sufficient to substantially define the shape of the walls of the cavity, and
   (d) from data determined in step (c), determining a three-dimensional model of the excision cavity.

24. The method of claim 23, wherein the ionizing radiation sources are switchable x-ray sources, and wherein step (c), taking a reading with the sensor, is accomplished by operating the sources at a high voltage level and measuring, via the sensor, the duration of time required for the sensor to detect a preselected dose for each source at each location.

25. The method of claim 23, wherein step (c), taking a reading with the sensor, is accomplished by determining dose received at the sensor from each of the sources over a preselected period of time.

26. A method for radiation therapy treatment of a patient, comprising:
   (a) inserting an applicator into a cavity in the patient's body, the applicator including a series of guides,
   (b) expanding the applicator to substantially fill the cavity, thereby placing the peripheral guides substantially at walls of the cavity adjacent to a volume to be treated with radiation,
   (c) with one or more ionizing radiation sources in peripheral ones of the guides and with a radiation sensor in a central one of the guides, moving the sources and sensor through the guides and taking a reading with the sensor for each of the sources at a plurality of locations along such movement, such locations being sufficient to substantially define the shape of the walls of the cavity,
   (d) from data determined in step (c), determining a three-dimensional model of the cavity,
   (e) making a radiation treatment plan for a volume to be treated immediately surrounding the cavity based on a radiation prescription and on the three-dimensional model of the cavity, for irradiation of the volume to be treated by use of such ionizing radiation sources and the applicator, and
   (f) executing the treatment plan by moving the ionizing radiation sources through the peripheral guides of the applicator with appropriate dwell times such that substantially prescribed dose of radiation is received in all regions of the volume to be treated.

27. The method of claim 26, further including placing extra-cavity sensors outside the cavity in critical areas where radiation dose must be limited to avoid damage, and during execution of the treatment plan, monitoring dose received at such extra-cavity sensors to assure that dose is limited in the critical areas.

28. The method of claim 26, wherein during steps (a) to (c), extra-cavity sensors are placed outside the cavity in critical areas where radiation dose must be limited to avoid damage, and during step (c), taking readings at each extra-cavity sensor from the source or sources at said plurality of locations, and using data from such readings as input to and to modify the radiation treatment plan, so as to limit dose at such critical areas.

29. The method of claim 28, further including, during execution of the treatment plan, monitoring dose actually received at such extra-cavity sensors to assure that dose is limited as needed in the critical areas.

30. A method for treating with x-ray radiation a volume within a living patient while avoiding damage to sensitive areas and limiting radiation dose where needed, comprising:
   (a) placing at least one x-ray sensor adjacent to the volume to be treated, in an applicator,
   (b) placing an array of switchable x-ray sources at positions surrounding the sensor in the applicator and adjacent to the volume to be treated,
   (c) calibrating the plurality of x-ray sources by switching each source on and off in turn, with the sources clustered closely around the sensor, and determining the dose from each of the x-ray sources,
   (d) expanding the applicator within the volume to be treated, so as to spread the array of x-ray sources outwardly as the applicator expands, thus spacing each source generally radially away from the sensor,
   (e) placing additional x-ray sensors outside the volume to be treated, so as to monitor x-ray radiation received at various sites outside the volume to be treated,
   (f) moving the x-ray sources and the sensor through the volume to be treated, turning the various x-ray sources of the array on and off in turn, and detecting the radiation from each of such sources using the x-ray sensor within the volume,
   (g) calculating the relative positions of all of the x-ray sources and the x-ray sensor using information obtained from step (f),
   (h) making a treatment plan for the volume to be treated, based on x-ray radiation dose prescribed for various regions of the volume to be treated, and including a plan for moving the array of x-ray sources and the sensor to different positions along the volume to be treated, with on/off switching as needed for each of the x-ray sources, along the path of movement for the treatment plan,
   (i) executing the treatment plan by moving the x-ray sources and sensor through the volume to be treated, in accordance with the treatment plan, and controlling x-ray delivery from each of the x-ray sources of the array in accordance with the treatment plan, including switching each of the sources on and off as needed.

31. A method for treating with x-ray radiation a volume within a living patient, with monitoring and verification of dose, comprising:
   placing at least one x-ray source adjacent to the volume to be treated,
   placing a plurality of x-ray sensors adjacent to the volume to be treated,
   commencing irradiation of the volume to be treated using the x-ray source, in accordance with a treatment plan,
   during the radiation treatment, monitoring dose received at the sensors to represent dose received at the volume being treated, and feeding back dose information to a processor that controls the radiation treatment in accordance with the treatment plan, and modifying the treatment plan and the radiation being delivered, as the treatment continues, in response to the monitored dose information fed back to the processor.

32. The method of claim 31, wherein the x-ray source comprises an electronic x-ray source adjustable as to voltage and current, and the method adjusting reducing voltage to the x-ray source to adjust depth of penetration of radiation when needed as determined by the processor in response to the information fed from the sensor.

33. The method of claim 31, wherein the tissue to be treated is in a breast following resection of a tumor, and including positioning sensors on the skin at the exterior of the breast or interstitially in the patient.

34. A method for treating with x-ray radiation a volume within a living patient, with monitoring and verification of dose, comprising:
placing at least one x-ray source into the patient and adjacent to the volume to be treated,
placing at least one x-ray sensor adjacent to the volume to be treated,
commencing irradiation of the volume to be treated using the x-ray source, in accordance with a treatment plan,
during the radiation treatment, monitoring dose received at the sensor and feeding back dose information to a processor that controls the radiation treatment in accordance with the treatment plan, and
verifying with the processor that the radiation delivered to the volume has been in accordance with the treatment plan, using the sensed dose information fed back to the processor.

35. The method of claim 34, wherein the tissue to be treated is in a breast, following resection of a tumor, and including positioning sensors on the skin at the exterior of the breast.

36. The method of claim 34, wherein the x-ray source comprises an electronic x-ray source adjustable as to voltage and current.

37. An apparatus for brachytherapy radiation treatment, comprising:
an applicator having an applicator shaft,
a source of radiation onboard the applicator, and
a radiation dosimeter sensor onboard the applicator, in a position to measure radiation dose emitted from the radiation source and received at the dosimeter sensor during a procedure using the applicator inserted into a patient, and
a processor in communication with the dosimeter sensor onboard the applicator, the processor receiving dose information from the sensor during the procedure.

38. The applicator of claim 37, wherein the applicator includes an expandable balloon adapted to be inflated in an excision cavity.

39. The apparatus of claim 37, the radiation source being an electronic controllable x-ray source, the processor controlling the emission of radiation from the source.

40. A method for brachytherapy radiation treatment on a living patient, in tissue surrounding a body cavity resulting from resection of a tumor, with verification of dose delivery to tissue, comprising:
inserting an applicator into a cavity of the patient produced by resection of a tumor, adjacent to a volume of tissue to be treated,
placing at least one radiation sensor adjacent to the volume to be treated,
treating the volume by emitting radiation from an x-ray source carried by the applicator, in accordance with a treatment plan,
before the treatment plan is completely carried out, monitoring dose received at the at least one sensor, and transmitting information on received dose to a processor, and with the processor and using the received dose information, verifying whether radiation treatment in the volume of tissue is according to the treatment plan.

41. A method for brachytherapy radiation treatment on a living patient, with verification of dose delivery to tissue, comprising:
inserting an applicator into a cavity or tissue of the patient, adjacent to a volume of tissue to be treated,
placing a series of radiation sensors adjacent to the volume to be treated, including sensors outside the applicator and on the applicator,
treating the volume by emitting radiation from an x-ray source carried by the applicator, in accordance with a treatment plan,
before the treatment plan is completely carried out,
monitoring dose received at the at least one sensor, and transmitting information on received dose to a processor, and with the processor and using the received dose information, verifying whether radiation treatment in the volume of tissue is according to the treatment plan.

42. The method of claim 41, including sensors outside the patient.

43. A method for brachytherapy radiation treatment on a living patient, with verification of dose delivery to tissue, comprising:
inserting an applicator into a cavity or tissue of the patient, adjacent to a volume of tissue to be treated,
placing at least one radiation sensor adjacent to the volume to be treated,
treating the volume by emitting radiation from an x-ray source carried by the applicator, in accordance with a treatment plan, the x-ray source comprising an electronic, controllable x-ray source, and
before the treatment plan is completely carried out, monitoring dose received at the at least one sensor, and transmitting information on received dose to a processor, wherein the processor controls the radiation emitted by the source, and with the processor and using the received dose information, verifying whether radiation treatment in the volume of tissue is according to the treatment plan.

44. The method of claim 43, further including the step of modifying the emitted radiation using the processor while the procedure continues, in response to the received dose information.

45. A method for brachytherapy radiation treatment on a living patient, with verification of dose delivery to tissue, comprising:
inserting an applicator into a cavity or tissue of the patient, adjacent to a volume of tissue to be treated,
placing at least one radiation sensor adjacent to the volume to be treated,
treating the volume by emitting radiation from an x-ray source carried by the applicator, in accordance with a treatment plan,
before the treatment plan is completely carried out, monitoring dose received at the at least one sensor, and transmitting information on received dose to a processor, and with the processor and using the received dose information, verifying whether radiation treatment in the volume of tissue is according to the treatment plan, and including modifying the radiation treatment before the treatment plan has been completed, in response to received dose information.

46. A method for brachytherapy radiation treatment on a living patient, with verification of dose delivery to tissue, comprising:

inserting an applicator into a cavity or tissue of the patient, adjacent to a volume of tissue to be treated, placing at least one radiation sensor adjacent to the volume to be treated, treating the volume by emitting radiation from multiple x-ray sources carried by the applicator, in accordance with a treatment plan, before the treatment plan is completely carried out, monitoring dose received at the at least one sensor, and transmitting information on received dose to a processor, and with the processor and using the received dose information, verifying whether radiation treatment in the volume of tissue is according to the treatment plan.

47. A system for treating with x-ray radiation a volume within a living patient, with monitoring and verification of dose, comprising:

at least one x-ray source, and an applicator for receiving and inserting the x-ray source into a patient, a plurality of x-ray radiation sensors located adjacent to the volume to be treated, and a processor in communication with the x-ray source and with the x-ray radiation sensors, and capable of carrying out a predefined radiation treatment plan, and including verification and control means for receiving dose information from the x-ray radiation sensors during a treatment and for modifying the radiation being delivered by the x-ray source during a treatment, in response to the sensed dose information fed to the processor from the x-ray radiation sensors.

48. The system of claim 47, wherein the at least one x-ray source comprise an electronic x-ray sources adjustable as to voltage and current, and including means in the processor for adjusting voltage to the x-ray source to adjust depth of penetration of radiation when needed as determined by the processor in response to the information fed from the sensor.

49. The system of claim 47, wherein the applicator includes an expandable balloon adapted to be inflated in a space within a patient, the x-ray source being within the balloon.

50. A method for determination of a prescribed radiation therapy treatment plan for treating selected tissue in a patient utilizing an ionizing radiation mapping source with known radiation absorption characteristics, comprising:

placing an applicator comprising at least one sensor adjacent to the tissue to be treated, placing at least one radiation source adjacent to the tissue to be treated such that the source is essentially in contact with the surface of the tissue, incrementally moving the source through a known sequential series of tissue-contacting positions which, in the aggregate, define the surface of the tissue to be treated, monitoring incident radiation from the source at each of said sequential positions to determine distance from each of the source positions to the sensor, thus mapping the surface of the tissue, and computing treatment parameters for each of said sequential positions based on known absorption characteristics of an ionizing radiation treatment source to be used in treatment.

51. The method of claim 50, wherein the source and sensor are both moved such that mapping results essentially in a series of sequential transverse cross sections along an axis adjacent to the tissue to be treated.

* * * * *